(12) United States Patent  
Russo

(10) Patent No.: US 9,662,003 B2  
(45) Date of Patent: *May 30, 2017

(54) TRIANGULATION MECHANISM FOR A MINIMALLY INVASIVE SURGICAL DEVICE

(71) Applicant: Covidien LP, Mansfield, MA (US)

(72) Inventor: Mark Russo, Plantsville, CT (US)

(73) Assignee: Covidien LP, Mansfield, MA (US)

( * ) Notice: Subject to any disclaimer, the term of this patent is extended or adjusted under 35 U.S.C. 154(b) by 174 days.

This patent is subject to a terminal disclaimer.

(21) Appl. No.: 14/479,457

(22) Filed: Sep. 8, 2014

(65) Prior Publication Data

US 2014/0378765 A1 Dec. 25, 2014

Related U.S. Application Data

(63) Continuation of application No. 13/483,553, filed on May 30, 2012, now Pat. No. 8,845,517.

(60) Provisional application No. 61/501,282, filed on Jun. 27, 2011.

(51) Int. Cl.

| | | |
|---|---|---|
| A61B 1/04 | (2006.01) | |
| A61B 1/32 | (2006.01) | |
| A61B 1/313 | (2006.01) | |
| A61B 17/34 | (2006.01) | |
| A61B 34/20 | (2016.01) | |
| A61B 1/00 | (2006.01) | |
| A61B 17/29 | (2006.01) | |

(52) U.S. Cl.
CPC ............. *A61B 1/32* (2013.01); *A61B 1/3132* (2013.01); *A61B 17/3423* (2013.01); *A61B 34/20* (2016.02); *A61B 2017/2905* (2013.01); *A61B 2017/2906* (2013.01); *A61B 2017/3429* (2013.01)

(58) Field of Classification Search
CPC ....... A61B 1/313; A61B 1/32; A61B 17/0218; A61B 17/0293; A61B 17/3423; A61B 2017/2908; A61B 1/3132; A61B 2017/2905; A61B 17/2906; A61B 17/3429
USPC ................................ 600/114, 115, 204, 201
See application file for complete search history.

(56) References Cited

U.S. PATENT DOCUMENTS

| | | |
|---|---|---|
| 4,898,577 A | 2/1990 | Badger et al. |
| 4,997,419 A | 3/1991 | Lakatos et al. |
| 4,998,916 A | 3/1991 | Hammerslag et al. |
| 5,007,434 A | 4/1991 | Doyle et al. |
| 5,306,245 A | 4/1994 | Heaven |
| 5,318,013 A | 6/1994 | Wilk |
| 5,441,483 A | 8/1995 | Avitall |
| 5,472,017 A | 12/1995 | Kovalcheck |
| 5,507,725 A | 4/1996 | Savage et al. |
| 5,743,880 A | 4/1998 | Hlavka |
| 6,068,621 A | 5/2000 | Balceta et al. |
| 6,554,794 B1 | 4/2003 | Mueller et al. |
| 7,250,027 B2 | 7/2007 | Barry |
| 7,527,620 B2 | 5/2009 | Long et al. |
| 7,637,903 B2 | 12/2009 | Lentz et al. |
| 7,682,319 B2 | 3/2010 | Martin et al. |

(Continued)

*Primary Examiner* — Timothy J Neal

(57) ABSTRACT

A surgical device including a seal anchor that includes leading and trailing portions. A plurality of ports longitudinally extends between the leading and trailing portions. The ports are adapted and configured to receive surgical objects therein. At least one of the surgical objects is a viewing instrument including a viewing portion. During a surgical procedure, surgical objects inserted in the other ports are selectively positionable with respect to the viewing instrument.

23 Claims, 6 Drawing Sheets

(56) References Cited

U.S. PATENT DOCUMENTS

| | | |
|---|---|---|
| 7,758,564 B2 | 7/2010 | Long et al. |
| 7,763,012 B2 | 7/2010 | Petrick et al. |
| 7,811,277 B2 | 10/2010 | Boulais |
| 8,845,517 B2 | 9/2014 | Russo |
| 2003/0149422 A1 | 8/2003 | Muller |
| 2004/0054322 A1 | 3/2004 | Vargas |
| 2005/0014995 A1 | 1/2005 | Amundson et al. |
| 2005/0234294 A1 | 10/2005 | Saadat et al. |
| 2007/0049966 A1 | 3/2007 | Bonadio et al. |
| 2007/0078302 A1 | 4/2007 | Ortiz et al. |
| 2007/0167680 A1 | 7/2007 | Miyamoto et al. |
| 2007/0208312 A1 | 9/2007 | Norton et al. |
| 2007/0270679 A1 | 11/2007 | Nguyen et al. |
| 2007/0299387 A1 | 12/2007 | Williams et al. |
| 2008/0009747 A1 | 1/2008 | Saadat et al. |
| 2008/0051631 A1 | 2/2008 | Dejima et al. |
| 2008/0097391 A1 | 4/2008 | Feinberg et al. |
| 2008/0188868 A1 | 8/2008 | Weitzner et al. |
| 2008/0188869 A1 | 8/2008 | Weitzner et al. |
| 2008/0281293 A1 | 11/2008 | Peh et al. |
| 2009/0005755 A1 | 1/2009 | Keith et al. |
| 2009/0012477 A1 | 1/2009 | Norton et al. |
| 2009/0024086 A1 | 1/2009 | Zhang et al. |
| 2009/0043299 A1 | 2/2009 | Racz |
| 2009/0157076 A1 | 6/2009 | Athas et al. |
| 2009/0192495 A1 | 7/2009 | Ostrovsky et al. |
| 2009/0198179 A1 | 8/2009 | Abbate et al. |
| 2009/0312696 A1 | 12/2009 | Copa et al. |
| 2010/0004633 A1 | 1/2010 | Rothe et al. |
| 2010/0081883 A1 | 4/2010 | Murray et al. |
| 2010/0121147 A1 | 5/2010 | Oskin et al. |

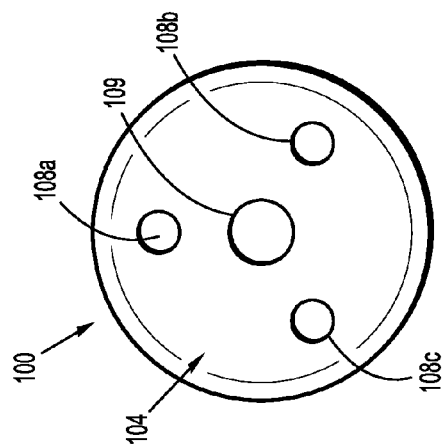
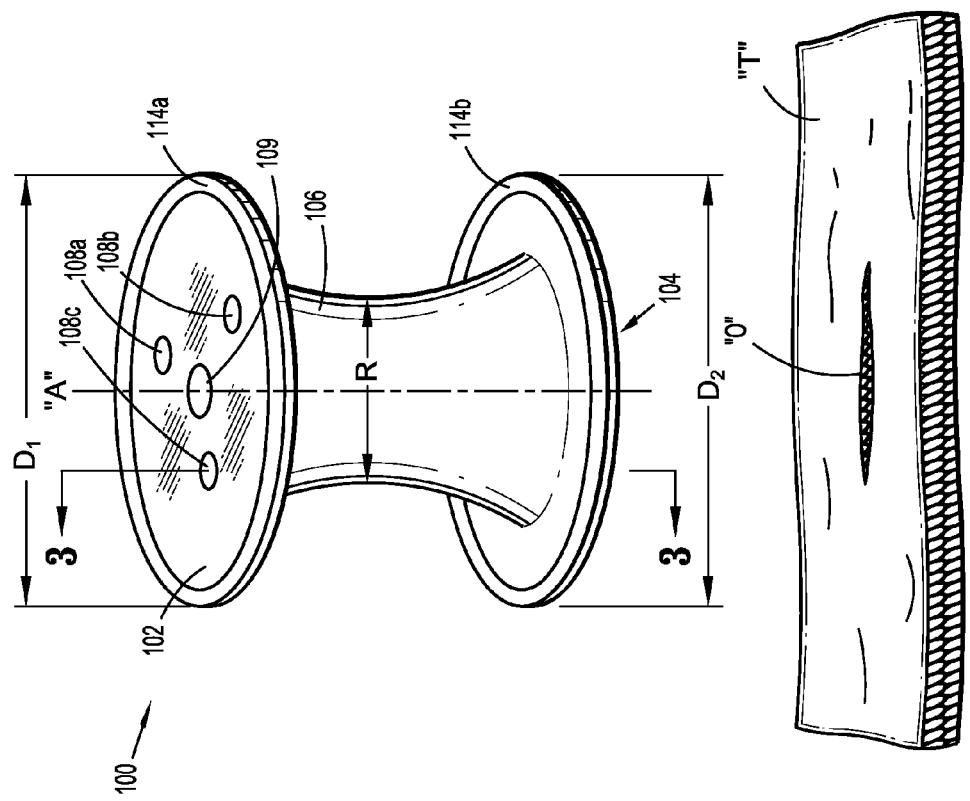

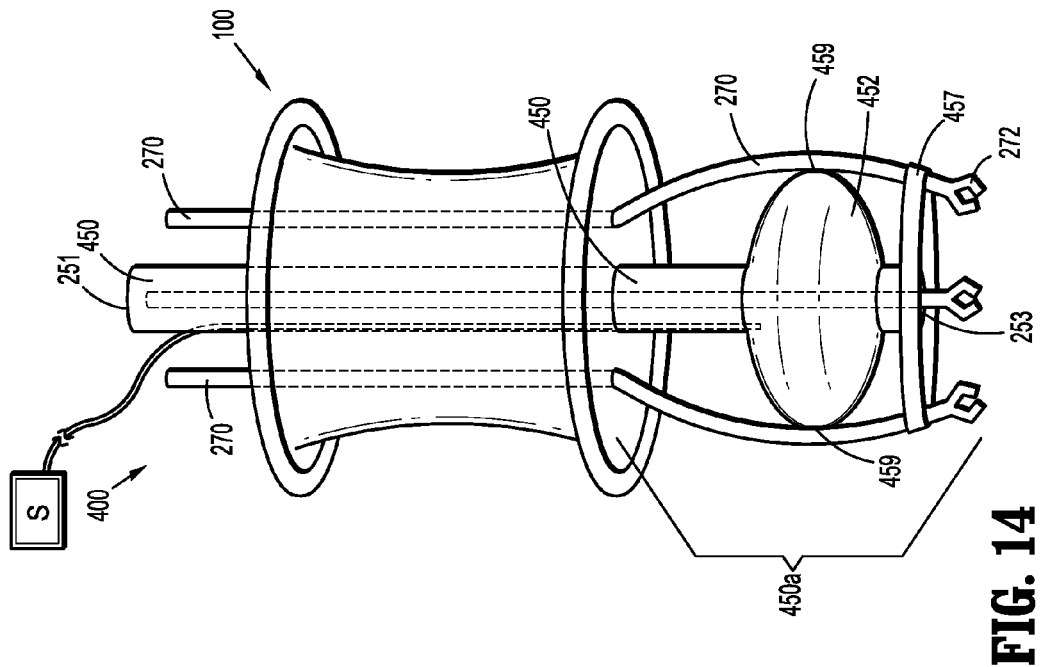
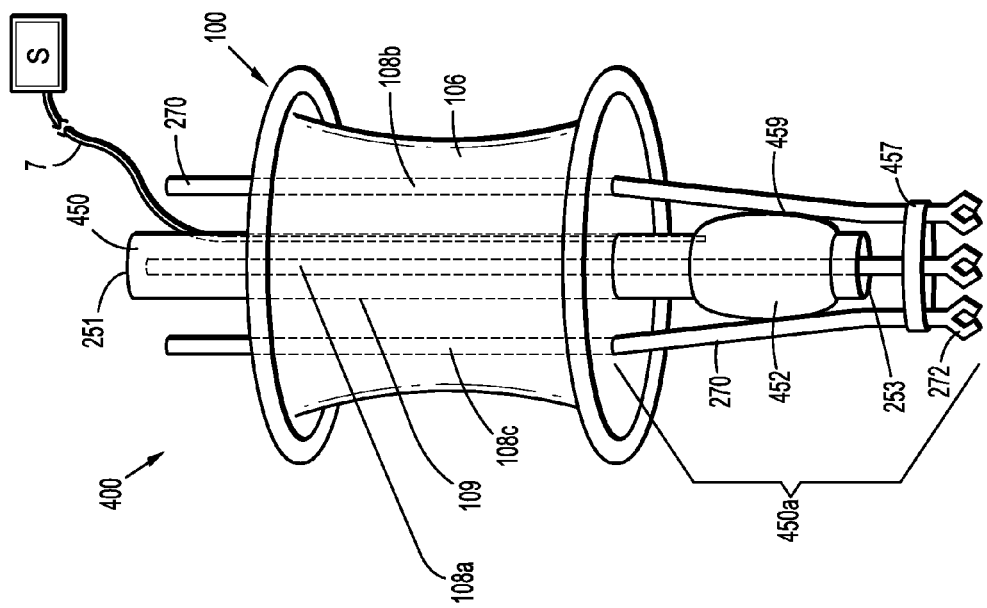

TRIANGULATION MECHANISM FOR A MINIMALLY INVASIVE SURGICAL DEVICE

CROSS-REFERENCE TO RELATED APPLICATIONS

This application is a continuation of U.S. patent application Ser. No. 13/483,553 filed May 30, 2012, now U.S. Pat. No. 8,845,517, which claims benefit of U.S. Provisional Application No. 61/501,282 filed Jun. 27, 2011, and the disclosures of each of the above-identified applications are hereby incorporated by reference in their entirety.

BACKGROUND

Technical Field

The present disclosure relates generally to a surgical device for use in a minimally invasive surgical procedure. More particularly, the present disclosure relates to a surgical portal device adapted and configured to receive surgical instruments therein, and to reposition the distal ends of the surgical instruments that are placed within the surgical portal device.

Background of Related Art

A minimally invasive surgical procedure is one in which a surgeon enters a patient's body through one or more small openings in the patient's skin or a naturally occurring opening (e.g., mouth, anus, or vagina). As compared with traditional open surgeries, minimally invasive surgical procedures have several advantages and disadvantages. Minimally invasive surgeries include arthroscopic, endoscopic, laparoscopic, and thoracic surgeries. Advantages of minimally invasive surgical procedures over traditional open surgeries include reduced trauma and recovery time for patients.

However, some disadvantages include a lack of direct visualization of the surgical site and reduced dexterity of instruments, as compared to traditional open surgeries. In particular, the simultaneous manipulation of the viewing instrument and surgical instruments that are inserted into the opening may be complicated. One complication arises from the difficulty in visualizing surgical instruments on a monitor that is operably coupled to the viewing instrument.

One surgical technique used to increase the ability of the surgeon to visualize and access critical anatomy is triangulation. Triangulation is a principle in which the positioning of the surgical instruments may be determined by having known initial positions of the instruments with respect to a given point, e.g., another device or instrument, and tracking the change in position from that initial position. One method of triangulation involves holding the surgical instrument and the viewing instrument so that their tips form the apex of an imaginary triangle. By knowing the initial positions of surgical instruments with respect to a given point and by tracking the change in position, the coordinates of the surgical instruments are determinable.

In conventional minimally invasive surgical procedures, triangulation is achieved through insertion of multiple instruments through multiple openings. In most minimally invasive surgical procedures through a single incision, straight and rigid surgical instruments are inserted through a single incision. To control the instruments, a surgeon often crosses his hands. The lack of triangulation makes visualization and access of critical anatomy potentially difficult.

Furthermore, the placement of multiple instruments through a single incision increases the potential of interference among those instruments. It would be advantageous to space those instruments apart within the surgical site, without necessitating a larger incision.

Consequently, a continuing need exists for improved minimally invasive surgical devices.

SUMMARY

Disclosed herein is a surgical system for use during a minimally invasive surgical procedure. The surgical system includes a seal anchor member for positioning within a tissue tract accessing an underlying body cavity and a triangulation device including a viewing instrument and one or more surgical instruments. The viewing instrument includes a viewing portion. The one or more surgical instruments may be triangulated with respect to the viewing portion of the viewing instrument.

The seal anchor member defines a longitudinal axis and includes leading and trailing ends. A plurality of ports extends longitudinally between the leading and trailing ends. Each port is configured and adapted to receive surgical instruments therethrough. A lumen is substantially centrally positioned along a longitudinal axis of the seal anchor and is configured and adapted to receive a surgical instrument therethrough, e.g., a viewing instrument including a viewing portion. In an embodiment, the lumen may receive a tube through which a viewing instrument, e.g., an endoscope is placed. The surgical instruments placed within the ports are configured and adapted to transition between a condition in which distal portions of the surgical instruments are substantially parallel with respect to the longitudinal axis of the viewing instrument and a condition in which the distal portions of the surgical instruments are angled with respect to the longitudinal axis viewing instrument. The angling of the surgical instruments with respect to the longitudinal axis of the viewing instrument facilitates triangulation.

Embodiments of mechanisms to effect triangulation of surgical instruments with respect to a viewing instrument that are placed within a seal anchor member, such as that described above, are disclosed herein. In one embodiment, a tube is placed within the centrally disposed lumen of the seal anchor. The tube is dimensioned for the reception of a viewing instrument therein. The tube includes a threading disposed about the distal portion of the tube. The tube is dimensioned to accommodate reception of a viewing instrument therein. A linkage operably couples each of the surgical instruments to the tube. In particular, the linkage may include first and second arms that are pivotably connected to the surgical instruments and a collar that is positioned about the tube. The tube may include threading that corresponds to threading on the collar such that rotation of the tube effects axial translation of the collar with respect to the tube. As the collar axially translates, the linkage mechanism transitions between a first state in which the first and second arms are angled with respect to one another and a second state in which the which the angle between the first and second arms is equal to 180 degrees, i.e., the first and second arms are parallel (for example, the first and second arms may be coaxial). The transitioning of the linkage mechanism between the first and second states determines the distance between the viewing instrument and the surgical instruments and thereby determines whether the surgical instruments are bent or angled with respect to the longitudinal axis of the seal anchor member. In an embodiment, the viewing instrument, e.g., an endoscope may be placed within a tube.

In another embodiment, a band formed from a sufficiently compliant material is biased toward a first, enlarged diameter and is transitionable to a second smaller diameter. The band also has a plurality of intermediate diameters between the first and second diameters. The band is operably coupled to the surgical instruments. The force necessary to bend or angle the surgical instruments corresponds to the position of the surgical instruments within ports of the seal anchor member. In particular, distal translation of the surgical instruments facilitates transitioning of the band to the first enlarged diameter, thereby effecting bending of the surgical instruments.

In a still further embodiment, a tube includes a balloon that is radially expandable to exert a force upon surgical instruments radially positioned about the tube to effect angling or bending of the surgical instruments with respect to the tube.

These and other features of the current disclosure will be explained in greater detail in the following detailed description of the various embodiments.

BRIEF DESCRIPTION OF THE DRAWINGS

Various embodiments of the present disclosure are described hereinbelow with reference to the drawings, wherein:

FIG. 1 is a front perspective view of a seal anchor member shown in an expanded condition and positioned relative to tissue;

FIG. 2 is a top view of the seal anchor member of FIG. 1;

FIG. 13 is a perspective view of another embodiment of a triangulation system in accordance with the present disclosure shown in a first state; and FIG. 14 is a perspective view of the triangulation system of FIG. 13 shown in a second state.

DETAILED DESCRIPTION OF THE EMBODIMENTS

Figure 3:
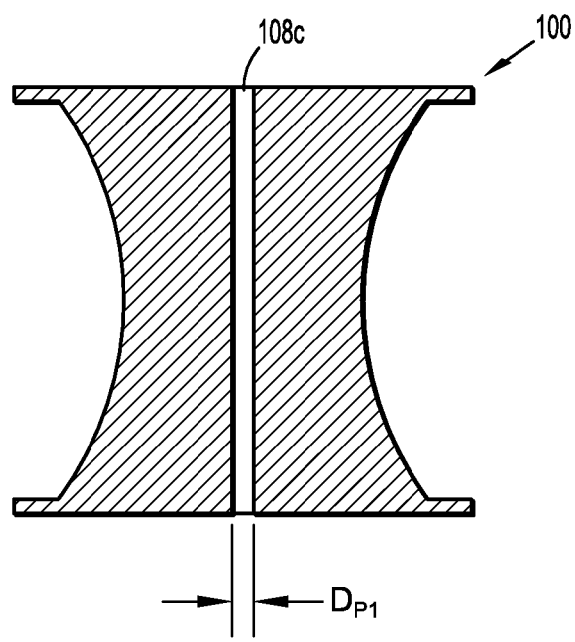
FIG. 3 is a cross-sectional view of the seal anchor member of FIG. 1 taken along section line 3-3 illustrating a port that extends longitudinally therethrough.

Particular embodiments of the present disclosure will be described herein with reference to the accompanying drawings. As shown in the drawings and as described throughout the following descriptions, and as is traditional when referring to relative positioning on an object, the term "proximal" will refer to the end of the apparatus that is closest to the clinician during use, and the term "distal" will refer to the end that is farthest from the clinician during use.

Figure 4:
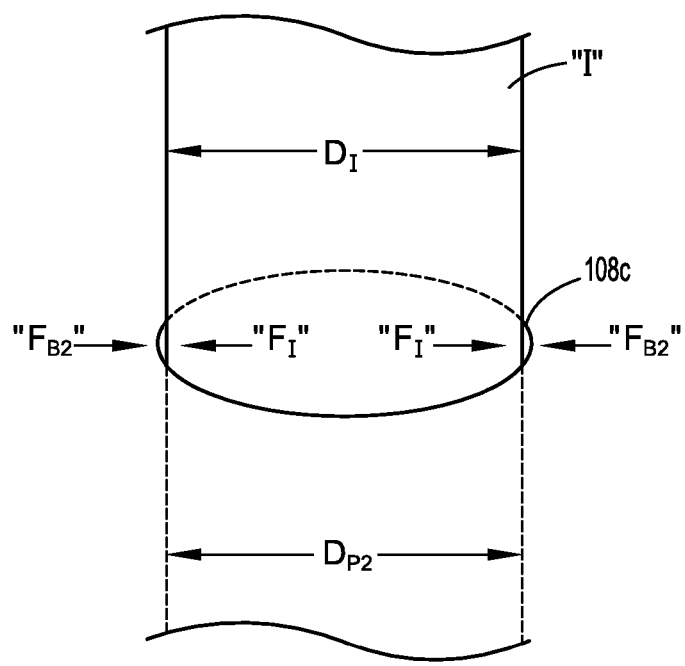
FIG. 4 is a view of the port of FIG. 3 with a surgical object inserted therethrough.
Figure 5:
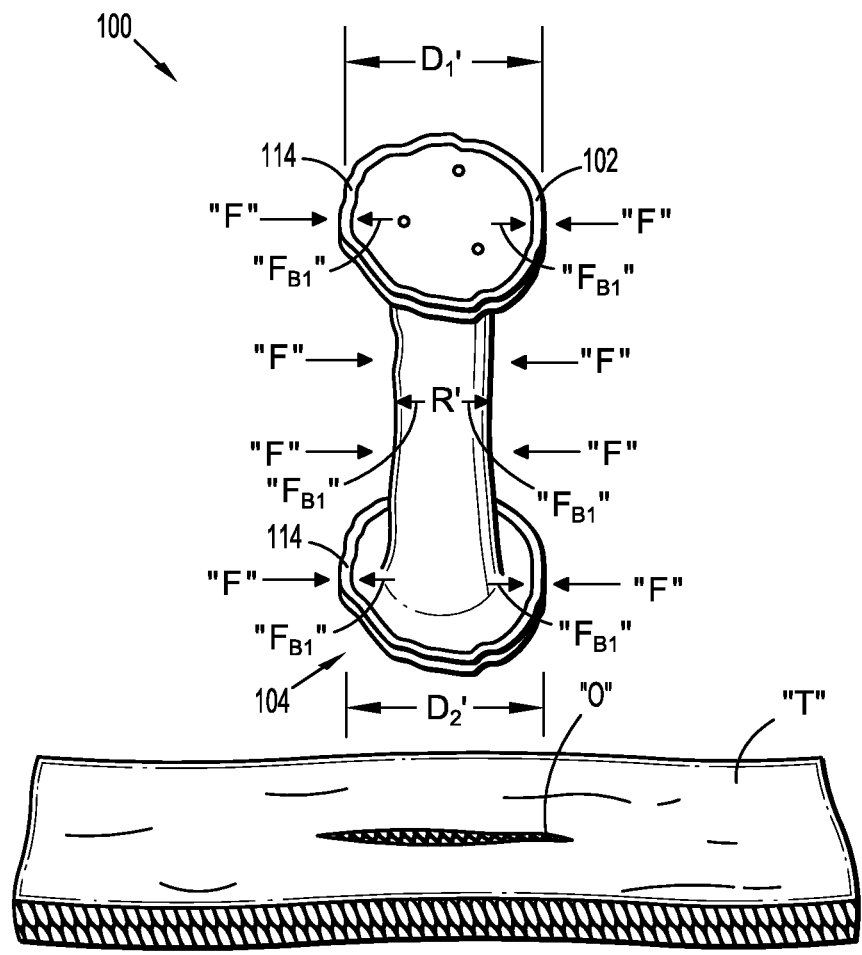
FIG. 5 is a perspective view of the seal anchor member of FIG. 1 shown in a compressed condition and prior to the insertion thereof into an opening in tissue.

With reference to FIGS. 1-5, a seal anchor member 100 will now be described. The seal anchor member 100 is configured and adapted to be placed within an opening "O", e.g., an incision or naturally occurring bodily orifice, within tissue "T" defining a tissue tract for accessing an underlying body cavity. The seal anchor member 100 may form a substantially seal with the tissue tract defined by the opening "O" to access an underlying body cavity while inhibiting the escape of insufflation gasses within the body cavity. To facilitate placement and securement of the seal anchor member 100 within the opening "O", the seal anchor member 100 is transitionable between an expanded condition (FIG. 1) and a compressed condition (FIG. 5). The seal anchor member 100 has an internal biasing force that biases the seal anchor member 100 toward the expanded condition.

The seal anchor member 100 defines a longitudinal axis "A" and includes respective trailing and leading sections 102, 104. An intermediate section 106 is disposed between the trailing and leading sections 102, 104. The seal anchor member 100 includes one or more ports 108a-c that extend longitudinally through the seal anchor member 100 and between the trailing and leading sections 102, 104. A lumen 109 extends longitudinally through the seal anchor member 100 and is substantially centrally disposed. The ports 108a-c and the lumen 109 may have the same or different diameters. For example, the ports 108a-c may have the same diameter, while the lumen 109 may have another diameter. Alternatively, the ports 108a-c may each have a different diameter.

In the expanded condition, the seal anchor member 100 is at rest and the respective radial dimensions $D_1$, $D_2$ of the trailing and leading sections 102, 104 of the seal anchor member 100, as well as radial dimension R of the intermediate portion 106, are such that insertion the seal anchor member 100 into the opening "O" is inhibited since the opening "O" defines a lesser radial dimension. However, in the compressed condition, trailing and leading sections 102, 104 of the seal anchor member 100, as well as the intermediate portion 106 are dimensioned for insertion into the opening "O".

The seal anchor member 100 includes ports 108a-c. A lumen 109 is central disposed between the ports 108a-c. Each of the ports 108a-c and the lumen 109 may be configured and adapted to receive surgical objects "I" (FIG. 3) therethrough in a substantially sealed relationship. In particular, the lumen 109 may receive an instrument, e.g., tube 250, therein.

Although discussed with respect to port 108c, the following is illustrative of how ports 108a-c and lumen 109 cooperate with an inserted instrument. As shown in FIG. 3, prior to the insertion of surgical object "I" within port 108c, the port 108c defines an initial radial dimension $D_{P1}$, which is generally about 0 mm to inhibit the escape of insufflation gas that may be present within the body cavity. For example, port 108c may be a slit extending the longitudinal length of seal anchor member 100 through proximal and distal sections 104, 104. Alternatively, the port 108c may define an opening within seal anchor member 100 having an initially open state.

Upon the introduction of surgical object "I", port 108c transitions to a second state in which port 108c defines a second, larger dimension $D_{P2}$ that substantially approximates diameter $D_I$ of surgical object "I" such that a substantially fluid-tight seal is formed therewith, thereby forming a sealed relationship between the port 108c and the surgical object "I". The sealed relationship between the port 108c and the surgical object "I" substantially inhibiting the escape of insufflation gas through port 108c of seal anchor member 100 when the surgical object "I" is inserted therein. $D_I$, and thus $D_{P2}$, will generally lie within the range of about 5 mm to about 12 mm, as these dimensions are typical of the surgical objects used during the course of minimally invasive procedures. However, a seal anchor member 100 including a port 108a-c may exhibit substantially larger, or smaller dimensions in the second state. In an embodiment, the seal anchor member 100 may be initially devoid of ports 108a-c, and may be created during use through the insertion of one or more surgical objects "I" through the seal anchor member 100.

As depicted in FIG. 5, as seal anchor member 100 is compressed under the influence of external force "F", an internal biasing force "$F_{B1}$" is created within seal anchor member 100 that is directed outwardly, opposing force "F". Internal biasing force "$F_{B1}$" endeavors to expand seal anchor member 100 and thereby return seal anchor member 100 to the expanded condition thereof. Accordingly, as long as seal anchor member 100 is subject to external force "F", seal anchor member 100 remains in the compressed condition. Upon the removal of external force "F", however, biasing force "$F_{B1}$" acts to return seal anchor member 100 to the expanded condition. In the compressed state, the seal anchor member 100 defines a reduced radial dimension. In particular, the trailing section 102 defines a radial dimension $D_1'$, the leading section 104 defines a radial dimension $D_2'$, and the intermediate section 106 defines a radial dimension R. The reduced radial dimension of the seal anchor member 100 facilitates insertion of the seal anchor member 100 into the opening "O" within tissue "T". Subsequent to insertion, the natural biasing force of the seal anchor member 100 transitions the seal anchor member 100 to the initial, greater radial dimension, thereby facilitating securing the seal anchor member 100 within the opening "O", and inhibiting the escape of insufflation gas.

The compressible material comprising seal anchor member 100 also facilitates the resilient transitioning of port 108a-c between its first closed state (FIG. 3) and its second state (FIG. 4). As previously discussed, prior to the insertion of surgical object "I", port 108a-c is in its first state in which port 108a-c defines a first or initial dimension $D_{P1}$. Port 108a-c may incorporate a slit extending the longitudinal length of seal anchor member 100. In this first state, port 108a-c is at rest and is not subject to any external forces. However, upon the introduction of surgical object "I" through port 108a-c as depicted in FIG. 4, the surgical object "I" exerts a force "$F_I$" upon port 108a-c that is directed radially outward. Force "$F_1$" acts to enlarge the dimensions of port 108a-c and thereby transition port 108a-c into the second state thereof in which port 108a-c defines a second, larger dimension $D_{P2}$ that substantially approximates the diameter $D_I$ of surgical object "I". Consequently, an internal biasing force "$F_{B2}$" is created that is directed radially inward, in opposition to force "$F_I$". Internal biasing force "$F_{B2}$" endeavors to return port 108a-c to reduce the internal dimension of port 108a-c and thereby return port 108a-c to the first state thereof. Internal biasing force "$F_{B2}$" is exerted upon surgical object "I" and acts to create a substantially fluid-tight seal therewith.

Referring again to FIG. 1, one or more positioning members 114a-b may be associated with either or both of trailing (or proximal) end 102 and distal (or leading) end 104, respectively, of seal anchor member 100. Positioning members 114a-b may be composed of any suitable biocompatible material that is at least semi-resilient such that positioning members 114a-b may be resiliently deformed and may exhibit any suitable configuration, e.g., substantially annular or oval. Prior to the insertion of seal anchor member 100, positioning members 114 are deformed in conjunction with the respective proximal and distal ends 102, 104 of seal anchor member 100 to facilitate the advancement thereof through tissue tract T (FIG. 5). Subsequent to the insertion of seal anchor member 100 within tissue tract T, the resilient nature of positioning members 114a-b allows positioning members to return to their normal, substantially annular configuration, thereby aiding in the expansion of either or both of the respective proximal and distal ends 102, 104 and facilitating the transition of seal anchor member 100 from its compressed condition to its expanded condition. Positioning members 114 also may engage the walls defining the body cavity to further facilitate securement of seal anchor member 100 within the body tissue. For example, positioning member 114a-b at leading end 104 may engage the internal peritoneal wall and positioning member 114a-b adjacent trailing end 102 may engage the outer epidermal tissue adjacent the opening "O" within tissue "T". In another embodiment of seal anchor member 100, one or more additional positioning members 114a-b may be associated with intermediate portion 106.

The seal anchor member 100 may be operably coupled to a triangulation device to form a triangulation system. An embodiment of a triangulation system including a triangulation device operably coupled to the seal anchor member 100 will now be described with reference to FIGS. 6-8. A triangulation system 200 (FIGS. 7 and 8) includes the seal anchor member 100 and a triangulation device 200A including surgical instruments 270 that are configured and adapted to be received within the seal anchor member 100 and to transition between at least two configurations. In a first configuration, at least one surgical instrument 270 may define an axis that is substantially parallel to the longitudinal axis "A" of the seal anchor member 100. In a second configuration, the at least one surgical instrument 270 defines an axis that is angled with respect to the longitudinal axis "A". It is preferable to insert or remove the triangulation system 200 while in the first configuration due to the relative smaller diameter of the triangulation system 200 while in the first configuration as compared to the triangulation system 200 while in the second configuration.

Figure 8:
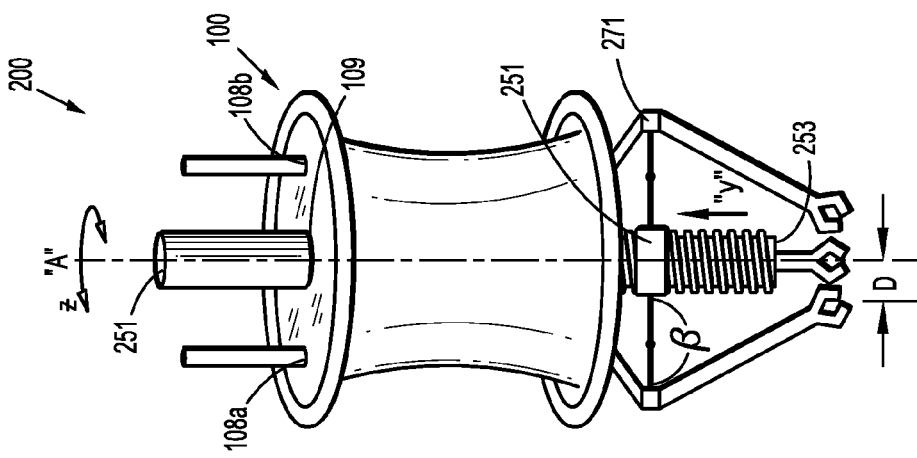
FIG. 8 is a perspective view of the triangulation system of FIG. 7 shown in a second condition.
Figure 6:
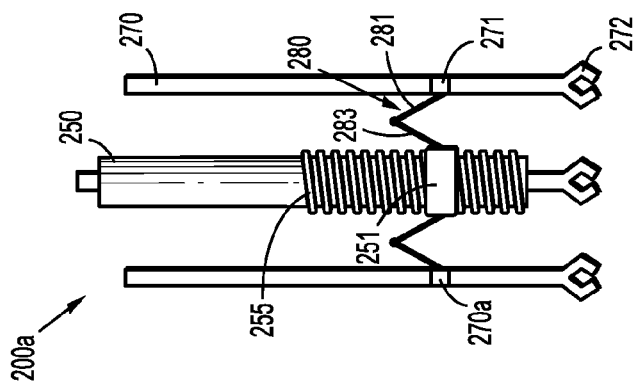
FIG. 6 is an embodiment of a triangulation device in accordance with the present disclosure.

As shown best in FIG. 6, the triangulation device 200A includes at least one surgical instrument 270 and a tube 250 including a viewing portion 253 (FIG. 8). The surgical instruments 270 are receivable within the ports 108a-c. The tube 250 is receivable within the lumen 109. The surgical instruments 270 are radially disposed about the tube 250.

The at least one surgical instrument 270 includes an end-effector 272. The surgical instrument 270 and/or the end-effector 272 may be substituted with a suitable instrument 270 and/or end-effector 272 as necessitated by the particular surgical procedure. The surgical instrument 270 may be hinged or may be formed from a compliant material such that the surgical instrument 270 may be angled with respect the longitudinal axis "A". In an embodiment, surgical instrument 270 may include a weakened or hinged region 270a such that application of a force in the weakened or hinged region effects bending of the surgical instrument at the weakened or hinged region.

By bending the surgical instrument 270, the distal end of the surgical instrument and therefore the end effector 272 is inwardly translated toward the center of the seal anchor 100 and substantially within the field of view of the viewing portion 253 of the viewing instrument 251. For example, the end effectors 272 of the surgical instruments 270 may be across the path of the viewing instrument 251. As shown in FIG. 6, surgical instrument 270 may include a hinge or a weakened region 270a to facilitate bending of the surgical instrument 270 in the desired direction, e.g., toward the viewing portion 253 of the tube 250. By placing the surgical instrument 270 in the field of view of the viewing portion 253, visualization of the surgical procedure is achieved.

Figure 7:
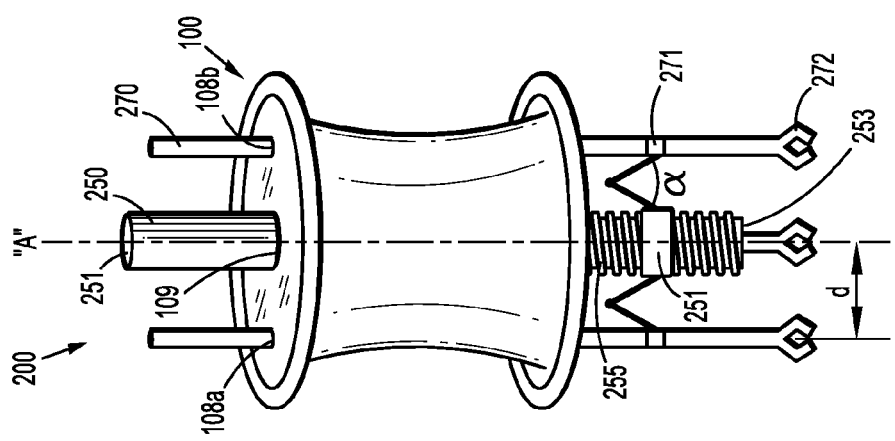
FIG. 7 is a perspective view of an embodiment of a triangulation system including the triangulation device of FIG. 6 shown operably coupled to the seal anchor member of FIG. 1 and shown in a first condition.

As shown in FIG. 6, the triangulation device 200A includes three surgical instruments 270 that are radially spaced a distance apart from the centrally disposed tube 250. Moreover, as shown in FIGS. 6 and 7, the surgical instruments 270 are transitionable between a first orientation in which the surgical instruments 270 define axes that are substantially parallel to one another (FIG. 7), and a second orientation in which the surgical instruments 270 define axes that are intersecting, i.e., the surgical instruments 270 are angled with respect to one another.

A linkage mechanism 280 operably connects the tube 250 and the surgical instruments 270. The linkage mechanism 280 facilitates transitioning of the transitioning of the triangulation system 200 between first and second configurations. As shown in FIGS. 7 and 8, the tube 250 may be rotated about axis "A" in the direction of directional arrow "Z". By rotating the tube 250, the angle of the surgical instruments 270 with respect to the longitudinal axis "A" is adjusted.

As shown in FIG. 6, the linkage mechanism 280 includes a collar 251 that is positioned about the tube 250 and is translatable along axis "A". The collar 251 includes an internal threading that corresponds to threading 255 disposed about the surface of the tube. In an embodiment, a viewing instrument may be manufactured to have threading on an exterior surface and may be substituted for the tube 250.

Each surgical instrument 270 may be formed from sufficiently compliant material such that application of a force against the surgical instrument 270 results in bending of the surgical instrument 270. Operably connecting each surgical instrument 270 to each other is a band 271 positioned about the surgical instrument 270. The band 271 is pivotably connected to a first arm member 281 that is pivotably connected to a second arm member 283. The second arm member 283 is pivotably connected to the collar 251.

In the first configuration, the first and second arm members 281, 283 define a first angle α with respect to one another such that the distance between the band 271 and the collar 251 and band 271 is a first distance d from one another. In the second configuration, the first and second arm members 281, 283 define a second angle β with respect to one another and the collar 251 and the band 271 is a second distance D from one another. The first and second arm members 281, 283 define intermediate angles between first angle α and second angle α, and the collar 251 and the band 271 define a plurality of distances between first distance d and second distance D. The surgical instruments 270 may also be axially translatable through the ports 108a-d in a synchronized or in an independent fashion. Moreover, the bands 271 may slide along the surgical instruments 270 thereby facilitating axial translation of the surgical instrument 270 that is independent from the axial translation of the tube 250. The threading 255 along the tube 250 may be uniformly spaced such that rotation of the tube 250 along or against directional arrow "Z" results in a predictable movement of the tubes 250. By knowing the initial coordinates of each surgical instrument 270, and in particular the end effector 272 of each surgical instrument 270, tracking of the coordinates, i.e., the position, of each surgical instrument 270 is achieved.

Another embodiment of a triangulation system will now be described with respect to FIGS. 9-12. Triangulation system 300 includes a triangulation device 300A, a tube 350 adapted to receive therein a viewing instrument 251 including a viewing portion 253, and seal anchor member 100. As shown best in FIG. 10, a flexible, compliant ring 380 operably connects surgical instruments 270. The ring 380 may be formed from a material having shape memory properties, e.g., a nickel titanium alloy (nitinol) to bias the ring toward an expanded state.

Figure 12:
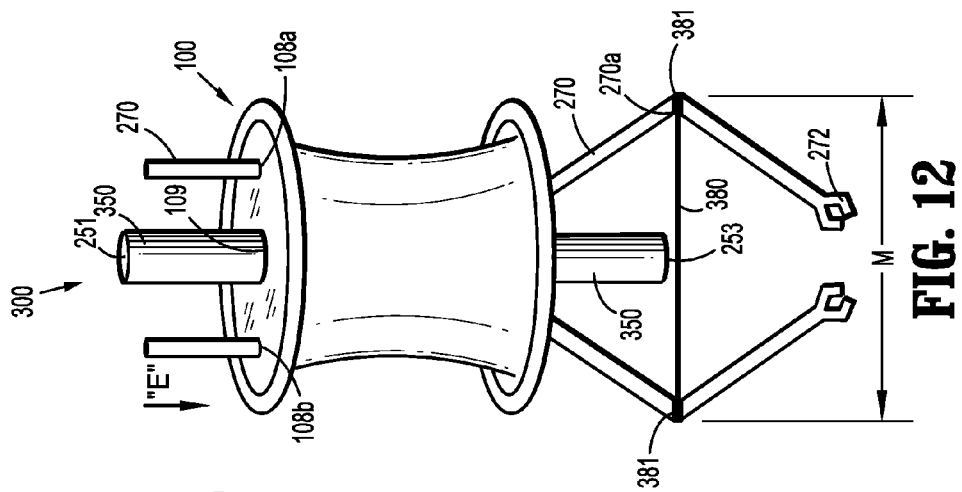
FIG. 12 is a perspective view of the triangulation system of FIG. 11 shown in a second condition.
Figure 11:
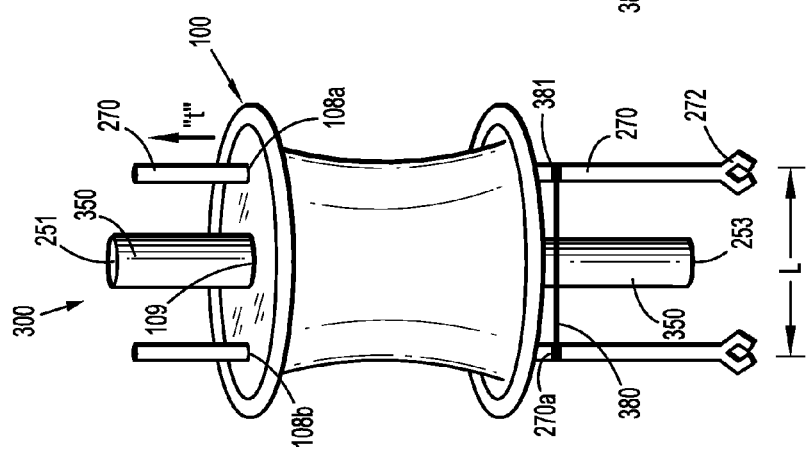
FIG. 11 is a perspective view of another embodiment of a triangulation system including the triangulation device of FIG. 9 shown in a first condition.
Figure 10:
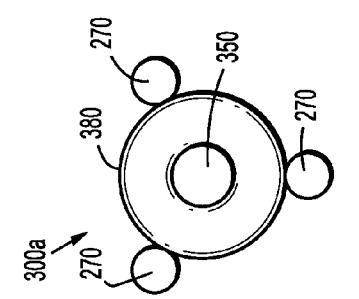
FIG. 10 is a top view of the triangulation device of FIG. 9.
Figure 9:
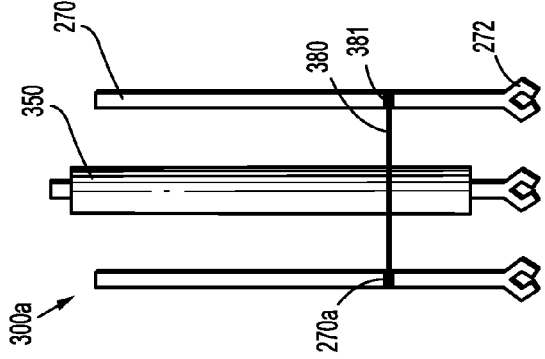
FIG. 9 is another embodiment of a triangulation device in accordance with the present disclosure.

In embodiments, the surgical instruments 270 and the ring 380 may be welded or adhesively bound together. As shown in FIG. 9, bands 381 are disposed about each surgical instrument and the bands 381 are coupled to the ring 380. The ring 380 is transitionable between a first diameter L and a second diameter M. The ring may be formed, for example, from a foam, plastic, or rubber material having sufficient compliance to transition between diameters L, M. The ring 380 may be biased toward the larger, second diameter M. The surgical instruments 270 are axially translatable in a proximal direction "C" and in a distal direction "E". When the surgical instruments 270 are drawn proximally (FIG. 11), the decreased distance between the distal end of the ports 108a-c means a greater force is needed to bend the surgical instruments 270 than is needed when the surgical instruments 270 are extended distally (FIG. 12). Translation of the surgical instruments 270 may effect a substantially synchronized or coordinated repositioning of each of the end effectors 272 of the surgical instruments 270 relative to the viewing portion 253 of the viewing instrument 251. By knowing the initial position, i.e., coordinates of the end effectors 272 of the surgical instruments 270 relative to the viewing portion 253 of the viewing instrument 251, tracking of the coordinates of each of the end effectors 272 is achievable.

The ring 380 applies a force to bend the surgical instruments 270 and to expand the surgical instruments 270 apart. The force applied by the ring 380 is counter to the biasing force of the surgical instruments 270 that are biased toward a straight configuration. When the surgical instruments 270 are drawn proximally (FIG. 11), the decreased distance between the distal end of the ports 108a-d means a greater force is needed to bend the surgical instruments 270 than is needed when the surgical instruments 270 are extended distally (FIG. 12) due to the increased leverage distance (moment arm). Accordingly, distal translation of the surgical instruments 270 through the ports 108a-c triangulates the instruments with respect to the viewing instrument 251 within the lumen 109 by bending the surgical instruments 270. Conversely, the proximal translation of the surgical instruments 270 through the ports 108a-c straightens the instruments 270, which due to the relatively smaller diameter of the triangulation system 300 (in the first configuration shown in FIG. 11) facilitates insertion and removal of the triangulation device 300 from the opening "O" within tissue "T" (FIG. 1).

In yet another embodiment, a triangulation system 400 includes the seal anchor member 100, and a triangulation device 450A including one or more surgical instruments 270 and a tube 450 adapted to receive the viewing instrument 251 including a viewing portion 253 therethrough. The tube 450 is placed within lumen 109 of the seal anchor member 100. The surgical instruments 270 are placed within ports 108a-c of the seal anchor member 100.

As shown in FIG. 13, the tube 450 includes a balloon 452 at a distal end thereof. A source of inflation "S" provides a source of inflation fluid (e.g., $CO_2$ or saline) to the balloon 452 through conduit 7. In a non-inflated state (FIG. 13), the balloon 452 does not exert sufficient force to overcome the biasing force of the surgical instruments 270. As the balloon inflates, the balloon 452 radially expands and exerts a force against the surgical instruments 270 to overcome the biasing force of the surgical instruments 270. As shown in FIG. 13, the surgical instruments 270 are inwardly biased such that the distal ends of the surgical instruments are pressed against the surface of the balloon 452. Insertion of the triangulation system 400 within an opening "O" within tissue "T".

In the inflated state, as shown in FIG. 14, the surgical instruments 270 are bent and are outwardly splayed apart. By spreading the surgical instruments 270 apart, interference between the surgical instruments 270 is inhibited.

In an embodiment, the internal bias and shape memory of the surgical instrument 270 facilitates placement of the end effectors 272 of the surgical instrument before the viewing portion 253 of viewing instrument 251 to facilitate visualization of the position of the end effectors 272. The surgical instruments 270 may be affixed to the balloon 452, for example, by an adhesive at fixation points 459. Furthermore, a band 457 may be placed about the surgical instruments 270, as shown in FIGS. 13 and 14. The band 457 may be placed at or near the distal end of the surgical instruments 270 such that inflation of the balloon 452 results in the inward angling of the end effects 272 of surgical instruments 270, thereby causing triangulation of the surgical instruments 270. In an embodiment, a length of shrink wrap may be placed about the surgical instruments 270, the internal bias of which causes the surgical instruments 270 to be secured to the balloon 452.

The inflation of the balloon 452 results in a uniform and predictable inflation of the balloon 452 such that the shape and size of the balloon 452 is known for a given volume of fluid, e.g., gas or liquid, within the balloon. Since the surgical instrument 270 is formed from a compliant material, the configuration of the surgical instrument 270 corresponds to the configuration of the balloon 452. The positioning of the surgical instruments 270 depends on the inflation of the balloon 452 and upon the positioning within the ports 108a-c, i.e., axial position of the surgical instrument 270 within each of the ports 108a-c. By tracking the axial position of the surgical instrument within the port 108a-c and the inflation level of the balloon 452, the position of the end effectors 272 of each surgical instrument 270 is determinable.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical system comprising:
   a seal anchor member for positioning within a tissue tract accessing an underlying body cavity, the seal anchor member defining a longitudinal axis and including leading and trailing ends, an intermediate section disposed between the leading and trailing ends, and a plurality of ports extending between the leading and trailing ends; and
   a triangulation device including:
      a rotatable member received in a first port of the plurality of ports in a sealing relation;
      at least one surgical instrument configured to be received in a second port of the plurality of ports in a sealing relation; and
      a linkage mechanism operably coupling the at least one surgical instrument and the rotatable member, wherein rotation of the rotatable member transitions the at least one surgical instrument between a first position in which the at least one surgical instrument is substantially parallel to the longitudinal axis of the seal anchor member and a second position in which at least a portion of the at least one surgical instrument defines an acute angle with respect to the longitudinal axis.

2. The surgical system of claim 1, wherein the linkage mechanism includes an arm member operably coupling the at least one surgical instrument and the rotatable member.

3. The surgical system of claim 2, wherein the linkage mechanism further includes a collar threadably coupled with the rotatable member, whereby rotation of the rotatable member causes movement of the collar along a length of the rotatable member.

4. The surgical system of claim 3, wherein the linkage mechanism further includes a band positioned about the at least one surgical instrument, the band pivotably connected to the arm member.

5. The surgical system of claim 4, wherein the arm member includes a first arm pivotably connected to the band and a second arm pivotably connected to the collar, the first and second arms pivotably coupled to each other.

6. The surgical system of claim 1, wherein the at least one surgical instrument includes a weakened region configured to bend upon application of a force thereto.

7. The surgical system of claim 1, wherein the at least one surgical instrument includes a hinge configured to bend upon application of a force thereto.

8. The surgical system of claim 1, wherein the at least one surgical instrument is formed of a compliant material.

9. The surgical system of claim 1, wherein the plurality of ports extend longitudinally between the leading and trailing ends of the seal anchor member.

10. The surgical system of claim 1, wherein the triangulation device further includes a viewing portion operatively associated with the rotatable member.

11. The surgical system of claim 1, wherein the at least one surgical instrument includes an end effector.

12. A surgical system, comprising:
   a seal anchor member for positioning within a tissue tract accessing an underlying body cavity, the seal anchor member including leading and trailing ends, the seal anchor member defining a plurality of ports extending between the leading and trailing ends; and
   a triangulation device including:
      a rotatable member configured to be received through a first port of the plurality of ports in a sealing relation; and
      at least one surgical instrument received in a second port of the plurality of ports in a sealing relation, the at least one surgical instrument operatively coupled with the rotatable member, wherein rotation of the rotatable member transitions the at least one surgical instrument between a first position in which the at least one surgical instrument is substantially parallel to a longitudinal axis defined by the rotatable member and a second position in which at least a portion of the at least one surgical instrument defines an acute angle with respect to the longitudinal axis.

13. The surgical system of claim 12, wherein the triangulation device further includes a viewing portion operatively associated with the rotatable member.

14. The surgical system of claim 12, wherein triangulation device further includes a linkage mechanism operably coupling the at least one surgical instrument and the rotatable member, the linkage mechanism including an arm member operably coupling the at least one surgical instrument and the viewing instrument.

15. The surgical system of claim 14, wherein the linkage mechanism further includes a collar threadably coupled with the rotatable member, whereby rotation of the rotatable member causes movement of the collar along a length of the rotatable member.

16. The surgical system of claim 15, wherein the linkage mechanism further includes a band positioned about the at least one surgical instrument, the band pivotably connected to the arm member.

17. The surgical system of claim 16, wherein the arm member includes a first arm pivotably connected to the band and a second arm pivotably connected to the collar, the first and second arms pivotably coupled to each other.

18. The surgical system of claim 12, wherein the at least one surgical instrument includes a hinge configured to bend upon application of a force thereto.

19. The surgical system of claim 12, wherein the at least one surgical instrument is formed of a compliant material.

20. The surgical system of claim 12, wherein at least one port of the plurality of ports extends longitudinally between the leading and trailing ends of the seal anchor member.

21. The surgical system of claim 12, wherein the at least one surgical instrument is disposed radially about the rotatable member.

22. The surgical system of claim 12, wherein the at least one surgical instrument includes an end effector.

23. The surgical system of claim 12, wherein the at least one surgical instrument includes a weakened region configured to bend upon application of a force thereto.

* * * * *